United States Patent [19]

Blaylock et al.

[11] Patent Number: 5,211,932
[45] Date of Patent: May 18, 1993

[54] CARBON BLACK PROCESS CONTROL SYSTEM

[75] Inventors: Charles R. Blaylock, Pampa; Melvin C. Dennis, White Deer; David J. Kaul, Pampa, all of Tex.; James L. Rice, Alpharetta, Ga.; Thomas L. Weaver, Chelmsford, Mass.

[73] Assignee: Cabot Corporation, Boston, Mass.

[21] Appl. No.: 763,479

[22] Filed: Sep. 20, 1991

Related U.S. Application Data

[63] Continuation of Ser. No. 376,792, Jul. 6, 1989, abandoned.

[51] Int. Cl.$^5$ .................................................. C09C 1/50
[52] U.S. Cl. .................................. 423/450; 423/DIG. 5
[58] Field of Search .................. 423/449, DIG. 5, 450, 423/449.1

[56] References Cited

U.S. PATENT DOCUMENTS

| | | | |
|---|---|---|---|
| 3,005,688 | 10/1961 | Williams | 23/259.5 |
| 3,350,173 | 10/1967 | Colby, Jr. et al. | 23/209.4 |
| 3,390,960 | 7/1968 | Forseth | 23/209.4 |
| 3,471,260 | 10/1969 | Lehr et al. | 23/209.4 |
| 3,592,599 | 7/1971 | Gohlke et al. | 23/209.4 |
| 3,636,148 | 1/1972 | Slagel | 264/40 |
| 3,734,999 | 5/1973 | Dollinger | 423/450 |
| 3,865,925 | 2/1975 | Mills | 423/450 |
| 3,993,447 | 11/1976 | Buss et al. | 23/259.5 |
| 4,080,434 | 3/1978 | Buss et al. | 423/450 |
| 4,093,705 | 6/1978 | Kraus et al. | 423/450 |
| 4,237,092 | 12/1980 | Lewis | 422/62 |
| 4,251,221 | 2/1981 | Austin | 23/230 A |
| 4,256,720 | 3/1981 | Kallenberger | 423/449 |
| 4,259,308 | 3/1981 | Kallenberger et al. | 423/449 |
| 4,296,087 | 10/1981 | Lewis | 423/449 |
| 4,311,672 | 1/1982 | Kallenberger | 422/150 |
| 4,313,723 | 2/1982 | Kallenberger et al. | 432/37 |
| 4,355,016 | 10/1982 | Stacy et al. | 423/450 |
| 4,390,347 | 6/1983 | Dille et al. | 48/197 R |
| 4,436,698 | 3/1984 | Stacy et al. | 422/62 |
| 4,636,375 | 1/1987 | Rothbühr | 423/450 |
| 5,049,369 | 9/1991 | Howell | 423/449 |

FOREIGN PATENT DOCUMENTS

| | | | |
|---|---|---|---|
| 55-114953 | 9/1980 | Japan | 422/62 |
| 89960 | 6/1980 | U.S.S.R. | 63/02 |

Primary Examiner—Gary P. Straub
Assistant Examiner—Stuart L. Hendrickson
Attorney, Agent, or Firm—Lawrence A. Chaletsky; Harry J. Gwinnell

[57] ABSTRACT

A carbon black process control system measures input variables such as feedstock flow rate, feedstock quality, air flow rate, air humidity, air temperature, fuel flow rate, fuel quality, and/or potassium additive solution flow rate at spaced intervals while the carbon black reactor is operating. Then, at spaced intervals in time one or more output variables of the carbon black, such as iodine number and/or DBP, are predicted in accordance with a prediction algorithm based on the values of the measured input variables. Then, at spaced intervals in time the predicted values of the output variables, such as iodine number and/or DBP, are averaged. Based on the average values of the predicted output variables, one or more input variables are then adjusted to achieve goal values of the predicted output variables, and thus obtain carbon black of substantially consistent quality. The predicted output variables are also laboratory measured from samples of the carbon black produced at spaced intervals in time while the carbon black reactor is operating. Then, based on both the predicted values and measured values of the output variables, the prediction algorithm is adjusted to improve the accuracy of the prediction of the output variables, and thus produce carbon black of substantially consistent quality.

28 Claims, 6 Drawing Sheets

CARBON BLACK PROCESS CONTROL SYSTEM

This application is a continuation of application Ser. No. 07/376,792, filed Jul. 6, 1989, now abandoned.

FIELD OF THE INVENTION

The present invention relates to process controls and, more particularly, to process controls for controlling the production of carbon black.

BACKGROUND INFORMATION

In the production of carbon black it is desirable to control certain output variables of the carbon black in order to produce carbon black of substantially consistent quality. Carbon black output variables that are often the focus of control are the iodine number and the DBP. Because the input variables and other physical parameters of carbon black production processes frequently change while the carbon black is produced, it has proved difficult to produce carbon black of substantially consistent quality. Input variables that frequently fluctuate during the carbon black production process are, for example, the air humidity and the fuel quality. Fluctuations in the input variables can have a significant influence on the carbon black output variables, such as iodine number and/or DBP. Likewise, other unmeasurable physical parameters frequently change during the carbon black production process, and also affect the carbon black output variables, such as iodine number and/or DBP.

In some known carbon black production systems, samples of the carbon black produced are taken at spaced intervals, for example, once every few hours of operation. Then, the output variables, such as iodine number and/or DBP, are measured for each sample. The operator then adjusts one or more input variables, such as the feedstock flow rate, after each sample is tested. The operator's adjustment is usually based on his or her own subjective experience with the particular carbon black production system, in order to try and bring the output variables, such as iodine number and/or DBP, back toward their goal values.

One problem with such known methods of controlling the production of carbon black is that the carbon black output variables, such as iodine number and/or DBP, are not controlled during the time intervals between samples. Therefore, if changes in the input variables or other physical parameters of the carbon black production system cause the value of the output variables, such as iodine number and/or DBP, to move outside of a desirable range of values, the change usually will not be noticed until the next sample is taken. As a result, a substantial amount of the carbon black produced may not fall within the customer's specifications. Yet another problem with such known methods of controlling the production of carbon black, is that such methods rely on the subjective analysis of the operator in order to adjust one or more input variables, based on the values of the laboratory measured output variables. As a result, input variable adjustments frequently may vary between operators and, therefore, result in an inconsistent quality in the carbon black produced.

It is an object of the present invention, therefore, to overcome the problems and disadvantages of known carbon black production systems.

SUMMARY OF THE INVENTION

The present invention is directed to a method of controlling the production of carbon black in a carbon black reactor, and comprises the following steps: (a) measuring at spaced intervals in time at least one input variable utilized in the production of carbon black while the carbon black reactor is operating; (b) employing at least one algorithm to predict at spaced intervals at least one output variable of the carbon black utilizing the at least one input variable measured during the spaced interval; (c) determining at spaced averaging intervals an average value of the at least one predicted output variable; and (d) adjusting at spaced intervals at least one of the input variables utilizing the difference between the average value of the at least one predicted carbon black output variable and a goal value of that output variable while the reactor is operating, in order to achieve the goal value of that output variable to obtain a substantially consistent quality of carbon black.

The method of the present invention preferably further comprises the following steps: (a) sampling at spaced intervals in time the carbon black produced while the carbon black reactor is operating; (b) measuring the at least one output variable from the sampled carbon black while the carbon black reactor is operating; and (c) adjusting the at least one algorithm by utilizing the measured value of the at least one output variable in order to more correctly predict that output variable.

In one embodiment of the present invention, the at least one predicted output variable is the iodine number, and the input variable adjusted at spaced intervals is the feedstock flow rate. In another embodiment of the present invention, the at least one predicted output variable is the DBP, and the input variable adjusted is the potassium additive solution flow rate.

In another embodiment of the present invention, the at least one algorithm is adjusted by utilizing a weighted mean of the error variance of the predicted values of the carbon black output variable during the period the carbon black sample is taken, and the error variance of the measured value of that output variable. The at least one algorithm is preferably adjusted by also employing at least one second algorithm for determining an optimum estimated output variable. The optimum estimate of the output variable is based on the weighted mean of the error variances and the difference between the measured value of the output variable and the average value of the predicted output variable during the period the sample was taken.

The present invention is also directed to an apparatus for controlling the production of carbon black in a carbon black reactor. The apparatus comprises metering means for measuring at spaced intervals in time at least one input variable utilized in the production of the carbon black while the carbon black reactor is operating. Computing means of the apparatus are coupled to the metering means for predicting at spaced intervals at least one carbon black output variable pursuant to at least one algorithm that utilizes the at least one input variable measured during the spaced interval. The computing means further determines at spaced averaging intervals an average value of the at least one predicted output variable over that spaced interval. The apparatus further comprises adjusting means coupled to the computing means for adjusting at spaced intervals pursuant to an adjusting algorithm the at least one input variable of the carbon black. The adjustment is based on the difference between the average value of the at least one predicted output variable over the spaced averaging interval and a goal value of that output variable, to achieve that goal value while the reactor is operating in order to obtain a substantially consistent quality of carbon black.

In another embodiment of the present invention, the apparatus further comprises sampling means for sampling at spaced intervals the carbon black produced while the carbon black reactor is operating, so that the at least one output variable can be laboratory measured. The computing means is responsive to the measured value of the at least one output variable for adjusting the at least one algorithm utilizing the measured value of the at least one output variable in order to more correctly predict that output variable.

Therefore, the method and apparatus of the present invention compensate for changes in the input variables and other physical parameters of the carbon black production system while the carbon black reactor is operating, in order to produce carbon black of substantially consistent quality. By measuring at spaced intervals at least one input variable, predicting at spaced intervals at least one output variable with an algorithm utilizing the at least one input variable, averaging at spaced averaging intervals the predicted output variables, and then adjusting at spaced intervals the at least one input variable by utilizing the average predicted value of the output variable, the method and apparatus of the present invention produces carbon black of substantially consistent quality. Likewise, by sampling the carbon black produced at spaced intervals, measuring the at least one output variable from the sampled carbon black, and adjusting the at least one algorithm by utilizing that measured value, the apparatus and method of the present invention can more accurately predict the output variable, and thus further produce carbon black of substantially consistent quality.

Other advantages and features of the present invention will become apparent in view of the following detailed description and drawings taken in connection therewith.

DETAILED DESCRIPTION

The carbon black process control system of the present invention compensates for variations in the physical parameters in a carbon black reactor by adjusting one or more input variables of the process, in order to control one or more output variables of the process, and thus produce carbon black of substantially consistent quality. The output variables of the carbon black that are controlled, for example, are iodine number and/or DBP.

Figure 1:
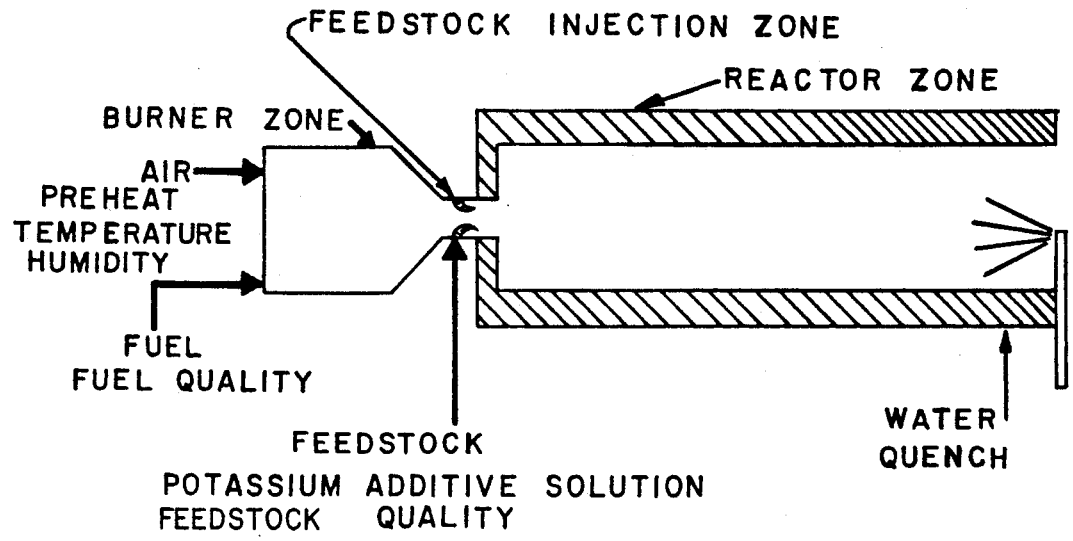
FIG. 1 illustrates schematically an example of a furnace carbon black reactor in which the process control system of the present invention may be employed.

In FIG. 1, an example of a furnace carbon black reactor, in which the process control system of the present invention may be employed, is illustrated schematically. The carbon black reactor shown is a three-stage reactor, including a burner zone, a feedstock injection zone, and a reactor zone. It should be noted, however, that the process control system of the present invention may be employed with any other type of carbon black reactor or process wherein a hydrocarbon feedstock is pyrolyzed with hot combustion gases to produce combustion products containing particulate carbon black. In the burner zone of the reactor in FIG. 1, a liquid or gaseous fuel is reacted with any type of suitable oxidant, preferably air, to form hot combustion gases. The resulting combustion gases are discharged from the downstream end of the burner zone and are caused to flow at a high velocity through the feedstock injection zone. A hydrocarbon feedstock in either gaseous, vapor or liquid form, which may be the same or different than the fuel utilized to form the combustion gas stream, is injected into the combustion gas stream in the feedstock injection zone, whereupon pyrolysis, or thermal decomposition of the hydrocarbon feedstock occurs. The reaction mixture of feedstock and combustion gases is then discharged into the reactor zone, where completion of the carbon black particle formation occurs. The reaction mixture is then quenched with a suitable fluid, usually water, in the end of the reactor zone to terminate the carbon black particle forming reaction. The reaction mixture is then further cooled and the solid carbon black particles are collected in a manner known to those skilled in the art.

The input variables that are analyzed by the carbon black process control system of the present invention are also illustrated schematically in FIG. 1. The input variables are each measured prior to injection into the burner zone or feedstock injection zone. The input variables include the feedstock flow rate, the fuel flow rate, the air flow rate, the air preheat temperature, the air humidity, the gas or other first stage fuel quality, the feedstock quality, and/or the potassium additive solution flow rate. Usually, only some of the input variables can be accurately controlled to control one or more output variables of the carbon black, such as iodine number and/or DBP. Typical controlled input variables are the feedstock flow rate, the fuel flow rate, the air flow rate, and/or the potassium additive solution flow rate.

In one embodiment of the present invention, the process control system calculates a predicted iodine number ($I_2No._p$) at spaced intervals, for example, every one to ten seconds. The predicted iodine numbers are calculated by an algorithm which is based, in part, on empirical test results for any given carbon black reactor geometry in which the process control system is employed. The predicted iodine numbers are then averaged ($I_2\text{No.}_{AVG}$) over spaced intervals, for example, every two minutes. Based on the average predicted iodine numbers, a controlled input variable, such as the feedstock flow rate, is automatically adjusted to achieve the goal iodine number ($I_2\text{No.}_{GOAL}$). Therefore, carbon black of substantially consistent quality can be produced regardless of changes in the measurable input variables of the carbon black reactor, such as air humidity and/or changes in the calculated input variables, such as fuel quality.

In accordance with an example of the present invention, the process control system is employed with a three-stage reactor as illustrated schematically in FIG. 1. The exemplary reactor uses a hydrocarbonaceous oil feedstock and natural gas fuel. It should be understood, however, that the process control system of the present invention may be used equally as well with any other type of reactor geometry, and any other type of feedstock and/or fuel. The predicted iodine numbers ($I_2\text{No.}_p$) may be calculated in accordance with the following iodine number algorithm:

$$I_2No._p = KC*OAc + KP*PC + KA*AIR + KT*CAT + KH*AH + KO \quad (1)$$

The algorithm constants are empirically determined for given carbon black reactor geometries. For example, the algorithm constants for a three-stage reactor, as illustrated in FIG. 1, might have different values from the algorithm constants for a two-stage reactor (not shown). The algorithm constants are defined as follows:

KC—overall combustion constant
KP—primary combustion constant
KA—air flow rate constant
KT—air preheat temperature constant
KH—air humidity constant
KO—system intercept constant The feedforward input variables are defined as follows:

OAC—overall combustion [%]
PC—primary combustion [%]
AIR—combustion air rate [KSCFH]
CAT—combustion air preheat temperature [°F.]
AH—air absolute humidity [lbs. water/thousand lbs. dry air]

The feedforward input variables are determined by measuring certain input variables of the carbon black reactor with metering instruments, while the reactor is operating. Immediately upon measuring the respective input variables, the feedforward input variables are calculated based on the following equations:

$$PC = \frac{AIR}{GAS*ATBG} * 100 \quad (2)$$

wherein:
AIR is the air flow rate [KSCFH] (standard cubic feet per hour, in thousands);
GAS is the gas flow rate [KSCFH]; and
ATBG is the air to burn gas ratio [SCF air/SCF gas], which is the stoichiometric value of the amount of air required to completely burn the corresponding volume of gas.

If the carbon black reactor uses a type of fuel other than gas, for example, a liquid hydrocarbon fuel, then the flow rate of that fuel would be indicated in equation (2) in place of the gas flow rate (GAS), and in the other equations described below where that term also appears. Likewise, the ATBG would be replaced in the same equations with the ratio of the stoichiometric value of the amount of air required to completely burn the corresponding amount of the type of fuel used. Similarly, if the carbon black reactor uses any suitable oxidant other than air, then the flow rate of that oxidant would be indicated in equation (2) in place of the air flow rate (AIR), and in the other equations described below where that term also appears.

$$OAC = \frac{AIR}{GAS*ATBG + OIL*ATBO} * 100 \quad (3)$$

wherein:
AIR is the air flow rate [KSCFH];
GAS is the gas flow rate [KSCFH];
ATBG is the air to burn gas ratio [SCF air/SCF gas];
OIL is the liquid hydrocarbon feedstock flow rate [gal./hr.]; and
ATBO is the air to burn oil ratio [KSCF air/gal oil], which is the stoichiometric value of the amount of air required to completely burn the corresponding volume of oil (a typical value is about 1.54 KSCF/gal. oil).

If the carbon black reactor uses feedstock other than a liquid hydrocarbonaceous feedstock, such as a gaseous hydrocarbonaceous feedstock, then the flow rate of that feedstock would be indicated in place of the oil feedstock flow rate (OIL), and in the other equations described below where that term also appears. Likewise, the ATBO would be replaced in the same equations with the ratio of the stoichiometric value of the amount of air required to completely burn the corresponding amount of the other type of feedstock used.

The air flow rate (AIR) and gas flow rate (GAS) are measured on-line by known metering instruments before injection into the burner zone of the carbon black reactor. The air and gas meters are preferably orifice-type meters that compensate for variations in the flowing pressures and temperatures in generating the flow rate signals. The ATBG is preferably calculated based on the input gas composition measured by a gas chromatograph (not shown). The gas chromatograph can either be employed to determine the gas composition periodically on-line or periodically off-line. Based on the updated gas composition, the ATBG value is correspondingly adjusted. Likewise, the specific gravity measurement of the gas used by the gas meter is also correspondingly adjusted based on the gas composition reading of the gas chromatograph. If the gas chromatograph measures the gas composition on-line, it ordinarily has the capability to update the ATBG value within the range of at least about every 2 to 10 minutes. The ATBO, on the other hand, ordinarily cannot be measured and updated on-line. Therefore, the ATBO value is preferably laboratory measured for each particular grade of feedstock or feedstock blends. The ATBO value might be updated, for example, before a production run or even once every several months.

The feedstock flow rate (OIL) is preferably measured by a Coriolis-type flow meter that measures the mass flow rate of feedstock, usually in lbs/hr, and the density of the feedstock, prior to injection into the feedstock injection zone of the reactor. The feedstock flow rate is preferably converted into a corrected volumetric flow rate, expressed in gallons per hour (gal./hr.). The combustion air preheat temperature (CAT) is measured by a thermocouple immediately prior to entry into the burner zone of the reactor. The air absolute humidity (AH) is measured by a humidity sensor of a type known in the art, and is expressed in units of lbs. of water/thousand lbs. dry air. The air absolute humidity measurements are preferably employed to serve two primary purposes. One purpose is to provide an updated feedforward input variable (AH) for the iodine number algorithm. The other purpose is to adjust the air flow rate (AIR) depending on the measured air absolute humidity (AH) to maintain a substantially constant dry air flow rate entering the burner zone of the reactor. A PID algorithm (proportional, integral, derivative control algorithm), of a type known in the art, is preferably employed to adjust the air flow rate depending on the updated air absolute humidity readings, in order to compensate for the amount of humidity in the air and thus maintain a substantially constant dry air flow rate.

The algorithm constants of the iodine number algorithm (equation (1)) are determined in accordance with a known process identification procedure using regression analysis, and are determined for given types of carbon black reactor geometries. Therefore, the values of the constants will likely be different for substantially different reactor geometries. A known software package, which includes the following components, "RS/1," "RS/Explore," and "RS/Discover," sold by BBN Software Products Corporation, of Cambridge, Mass., is preferably employed for performing the regression analysis procedure. The BBN Software can be used with a VAX minicomputer, manufactured by the Digital Equipment Corporation, of Maynard, Mass. The BBN Software facilitates the implementation of experimental design procedures, which are known to those skilled in the art, as well as regression analysis procedures, also known to those skilled in the art, and is not necessary, but simply provides a convenient means for carrying out such procedures.

In performing the regression analysis procedure, the input and output variables in the carbon black production process are identified. The input variables in relation to the iodine number are, for example, those illustrated in FIG. 1, including the feedstock flow rate, air flow rate, fuel flow rate, air preheat temperature and humidity, fuel quality (ATBG), and feedstock quality (ATBO). The output variable is the iodine number ($I_2$No.). Based on the input variables and output variable identified, a series of experiments is designed to identify the parameters of the algorithm by employing preferably the BBN Software in a VAX minicomputer. The series of experiments is then run on a carbon black reactor having the type of reactor geometry for which the algorithm will be used. Therefore, the regression analysis procedure will likely provide constants that have different values for different types of reactor geometries. At different stages during the experiments, changes are made to the input variables in a manner prescribed by the designed experiments. Based on the experiments, a set of input and corresponding output data is collected. The regression analysis procedure is then performed on the set of data to identify the empirically determined constants of the iodine number algorithm (equation (1)).

In accordance with one example of the present invention, pursuant to the above-described regression analysis procedure, the following constants were empirically determined for a three-stage reactor geometry similar to that illustrated schematically in FIG. 1:

| | |
|---|---|
| KC = 12.5 | KT = 0.094 |
| KP = −0.123 | KH = −0.238 |
| KA = −0.184 | KO = −201 (approximately) |

Therefore, in accordance with one embodiment of the present invention, the input variables necessary to determine the feedforward input variables of the iodine number algorithm (equation (1)) are measured about once every second. Then, based on those measurements, the iodine number algorithm is solved about once every second to generate a new predicted iodine number ($I_2$No.$_p$). Then, at spaced averaging intervals, for example, about every two minutes, the predicted iodine numbers calculated over that interval are averaged ($I_2$No.$_{AVG}$). A controlled input variable, such as the feedstock flow rate (OIL), is then automatically adjusted at the end of each averaging interval depending on the difference between the average predicted iodine number ($I_2$No.$_{AVG}$) and the iodine number set point or goal iodine number ($I_2$No.$_{GOAL}$), in order to achieve the goal iodine number. It should be noted, however, that one or more other input variables, such as the AIR and/or GAS can be adjusted instead of the feedstock flow rate (OIL) to achieve the goal iodine number ($I_2$No.$_{GOAL}$).

The relationship between the iodine number and the OAC is the primary adjustment relationship. The OAC is a calculated control variable as opposed to a measured control variable. As will be described below, the equation defining the OAC includes as its terms the AIR, the GAS, and the OIL. Therefore, based on the relationship between the iodine number and the OAC, the appropriate changes in the preferred measured control variable, OIL, can be derived to achieve the goal iodine number ($I_2$No.$_{GOAL}$). The feedstock flow rate (OIL) is the preferred input variable to control, because, for one reason, it appears in only one term of the iodine number algorithm and, therefore, the adjustment procedure can be relatively simple and straightforward.

The new feedstock flow rate (OIL$_{NEW}$), that is required to achieve the goal iodine number ($I_2$No.$_{GOAL}$), is estimated based on the following relationship between the iodine number and the OAC:

$$\Delta I_2 No. = KC \cdot \Delta OAC \qquad (4)$$

wherein:
$\Delta I_2$No. is the $I_2$No.$_{GOAL}$ minus the two minute average (or other spaced interval) of the $I_2$No.$_p$ ($I_2$No.$_{AVG}$);
$\Delta$OAC is the new OAC (OAC$_{NEW}$) required to achieve the $I_2$No.$_{GOAL}$ minus the two minute average of the measured OAC (OAC$_{AVG}$); and
KC is the overall combustion constant of the iodine number algorithm.

Equation (4) is adapted from the partial derivative of the iodine number algorithm (equation (1)) with respect to the OAC. The new feedstock flow rate (OIL$_{NEW}$) is then determined based on the following equations:

$$OAC_{NEW} = \frac{\Delta I_2 No.}{KC} + OAC_{AVG} \quad (5)$$

$$OAC_{NEW} = \frac{AIR_{AVG}}{GAS_{AVG} * ATBG + OIL_{NEW} * ATBO} * 100 \quad (6)$$

Equations (5) and (6) are then solved for $OIL_{NEW}$ as follows:

$$OIL_{NEW} = \left[ \frac{100 * AIR_{AVG}}{ATBO*(\Delta I_2 No./KC + OAC_{AVG})} \right] - GAS_{AVG} * \frac{ATBG}{ATBO} \quad (7)$$

Accordingly, $OIL_{NEW}$ can then be calculated every two minutes (or other spaced interval) utilizing the average of the predicted iodine numbers ($I_2No._{AVG}$) calculated over that averaging interval, and the feedstock flow rate (OIL) can then be automatically adjusted in order to achieve the $I_2No._{GOAL}$.

The carbon black process control system of the present invention has as an additional feature, an off-line laboratory measurement procedure. At spaced intervals, while the carbon black reactor is operating, samples of the carbon black produced are taken and the iodine number of each sample is measured ($I_2No._{LAB}$) by known techniques. The measured iodine number ($I_2No._{LAB}$) and its known standard deviation ($SD_{LAB}$) are determined along with the average and standard deviation ($SD_p$) of the predicted iodine numbers ($I_2No._p$) for the period that the sample was taken. Then, depending on the values of the measured iodine number ($I_2No._{LAB}$), its test standard deviation ($SD_{LAB}$), and the average and standard deviation ($SD_p$) of the predicted iodine numbers ($I_2No._p$), the system intercept constant (KO) of the iodine number algorithm (equation (1)) is adjusted in order to calculate a more accurate predicted iodine number ($I_2No._p$), as will be hereinafter described in further detail. Thus, in accordance with the present invention, the accuracy of the iodine number control algorithm (equation (1)) itself can be systematically checked against the laboratory measured iodine number ($I_2No._{LAB}$) and improved while the carbon black reactor is operating. The off-line sampling feature of the present invention therefore compensates for unmeasured disturbances on the carbon black reactor that are not currently measured, or cannot be measured, as opposed to the measurable input variables, as described above.

In accordance with the present invention, a filter algorithm, preferably a Kalman filter algorithm, is applied to change the system intercept (KO) of the iodine number algorithm. The system intercept (KO) is changed based on the measured iodine number ($I_2No._{LAB}$) and the predicted iodine numbers ($I_2No._p$) determined during the interval that the carbon black sample is taken, in order to make the iodine number algorithm more correctly predict the iodine numbers. The iodine number of the carbon black sample ($I_2No._{LAB}$) is measured in a manner known to those skilled in the art, such as by a volumetric method of titrating the carbon black sample with an iodine solution. The iodine number test is preferably performed according to the iodine adsorption number test given by ASTM Designation: D1510-85. The sampling interval when the carbon black sample is taken is usually within the range of about 2 to 20 minutes.

In accordance with the sampling feature of the present invention, the best estimate of the error variance of the current predicted iodine numbers ($V_{IP}$), and the error variance of the laboratory measured iodine number ($V_{IL}$) are determined. The error variance is the square of the standard deviation of the iodine number. Therefore, $V_{IL}$ is the square of the standard deviation ($SD_{LAB}$) of the laboratory measured iodine number for the sample of carbon black ($I_2No._{LAB}$). Because usually only one laboratory measured iodine number ($I_2No._{LAB}$) is taken during each sample period, $V_{IL}$ is essentially a constant that is determined by a separate laboratory measured iodine number precision or reproducibility study, of a type known in the art. $V_{IL}$, therefore, is usually updated periodically, for example, once every several months, or when there is a change in the procedure for determining the laboratory measured iodine number ($I_2No._{LAB}$). $V_{IP}$ is the best estimate of the error variance of the current predicted iodine number ($I_2No._p$), as will be described in further detail below. $V_{IP}$ and $V_{IL}$ are thus each indications of the uncertainties in the respective iodine number determinations themselves.

Based on the error variances, $V_{IP}$ and $V_{IL}$, an iodine number Kalman filter gain ($K_I$), which, as will be described below, is then used to update the system intercept (KO) of the iodine number algorithm, is determined as follows:

$$K_I = \frac{V_{IP}}{V_{IP} + V_{IL}} \quad (8)$$

The Kalman filter gain ($K_I$), therefore, is essentially a weighted mean of the error variances ($V_{IP}$ and $V_{IL}$), which each reflect the degree of variation in two ordinarily noisy measurements ($I_2No._p$ and $I_2No._{LAB}$) The $I_2No._p$ and the $I_2No._{LAB}$ are usually different. Therefore, the Kalman filter gain ($K_I$) is, in effect, a weighting coefficient based on statistical information regarding the reliability of the two different measurements, $I_2No._p$ and $I_2No._{LAB}$, that indicates which measurement is more accurate. For example, if $K_I=1$, then there is a negligible error variance in the $I_2No._{LAB}$ and if $K_I=0$, then there is a negligible error variance in the $I_2No._p$.

Based on the Kalman filter gain ($K_I$), a Kalman filter algorithm is employed to determine a new optimum estimated iodine number ($I_2No._{FILTER}$), as follows:

$$I_2No._{FILTER} = I_2No._{AVG} + K_I*(I_2No._{LAB} - I_2No._{AVG}) \quad (9)$$

wherein $I_2No._{AVG}$ is the average of the predicted iodine numbers ($I_2No._p$) during the period that the sample was taken.

Then, based upon the new optimum estimated iodine number ($I_2No._{FILTER}$), a new system intercept constant ($KO_{NEW}$) for the iodine number algorithm is calculated as follows:

$$KO_{NEW} = KO_{OLD} + I_2No._{FILTER} - I_2No._{AVG} \quad (10)$$

It should be noted that a one point change, for example, in the system intercept constant (KO) corresponds to a one point change in the iodine number and, therefore, the numbers can be directly substituted into equation

(10) to solve for $KO_{NEW}$. Therefore, the system intercept constant (KO) is adjusted, each time the laboratory measured iodine number ($I_2No._{LAB}$) becomes available, in order to make the iodine number algorithm (equation (1)) more correct.

Turning again to the error variances, the best estimate of the true current error variance of the predicted iodine number ($V_{IP}(k+1)$) at time interval (k+1) and which, as will be described below, is employed to determine the Kalman filter gain ($K_f$), is determined as follows:

$$V_{IP}(k+1) = V_{IE}(k) + V_{IM}(k+1) \tag{11}$$

wherein:
- $V_{IP}(k+1)$ is the best estimate of the true current error variance of the current predicted iodine number ($I_2No._p$) at time interval (k+1);
- $V_{IE}(k)$ is the error variance of the previous L- optimum iodine number estimate ($I_2No._{FILTER}$) at time interval (k);
- $V_{IM}(k+1)$ is the error variance of the predicted iodine numbers ($I_2No._p$) at time interval (k+1) measured over last sample period.

The new Kalman filter gain ($K_f(k+1)$) is then determined from the error variances of the current predicted iodine numbers ($I_2No._p$) and the current laboratory measured iodine number ($I_2No._{LAB}$) as follows:

$$K_f(k+1) = \frac{V_{IP}(k+1)}{[V_{IP}(k+1) + V_{IL}(k+1)]} \tag{12}$$

$V_{IL}(k+1)$ is the error variance of the current laboratory measured iodine number ($I_2No._{LAB}$) and is defined as follows:

$$V_{IL}(k+1) = [PSD_{LAB}/100]^2 * I_2No._{GOAL} \tag{13}$$

$PSD_{LAB}$ is the percent standard deviation of the iodine number test as determined by a precision or reproducibility study, known in the art. Therefore, the new optimum Kalman filter gain ($K_f(k+1)$) is substituted into equation (9) above to solve for the new optimum predicted iodine number ($I_2No._{FILTER}$). The $I_2No._{FILTER}$ is then substituted into equation (10) above to solve for the new system intercept constant ($KO_{NEW}$) to make the iodine number algorithm more correctly predict the iodine number.

The error variance of the new optimum estimated iodine number ($V_{IE}(k+1)$ to be used in determining $V_{IP}(k+1)$ at the end of the next sample period ($V_{IE}(k)$ in equation (11) above) is then determined as follows:

$$V_{IE}(k+1) = \frac{V_{IP}(k+1) * V_{IL}(k+1)}{[V_{IP}(k+1) + V_{IL}(k+1)]} \tag{14}$$

In accordance with another embodiment of the present invention, the process control system is employed to control the structure of the carbon black. The structure of the carbon black is usually laboratory measured by a Dibutyl Phthalate Absorption Number ("DBP") given by ASTM Designation: D2414-86. The DB value therefore is an indication of the structure of the carbon black. There are, however, other suitable measures of carbon black structure that can equally be controlled by the process control system of the present invention. One way of controlling the DBP is by injecting a potassium additive solution (K+S), known in the art, preferably into the feedstock prior to injecting the feedstock into the feedstock injection zone of the reactor. The potassium additive solution (K+S) is then dispersed in the reaction mixture in the reactor zone, and thus has an ionic charge effect on the particles of carbon black formed. Therefore, usually, if a higher concentration of potassium additive solution (K+S) is injected into the feedstock, then there will tend to be less aggregation among the particles of carbon black formed.

In accordance with the present invention, predicted DBP values ($DBP_p$) are calculated at spaced intervals, for example, every one to ten seconds. The predicted DBP values ($DBP_p$) are calculated by a DBP algorithm which is based, in part, on empirical test results for any given carbon black reactor geometry in which the process control system is employed. The predicted DBP values are then averaged over spaced intervals, for example, every two minutes ($DBP_{AVG}$). Based on the average predicted DBP values ($DBP_{AVG}$), a controlled input variable, such as the potassium additive solution flow rate (K+S) is automatically adjusted to achieve the goal DBP value ($DBP_{GOAL}$).

The predicted DBP values ($DBP_p$) may be calculated in accordance with the following DBP algorithm:

$$DBP_p = (164.9 - 17.3*X)*F \text{ for } 0 < X < 1 \tag{15}$$

and $$DBP_p = (147.6 - 17.3*ln(X))*F \text{ for } X > 1 \tag{16}$$

wherein:
- X is the concentration of the potassium ion (K+) in the feedstock [gm K+/100 gal. oil]; and
- F is a scale factor calculated to adjust the algorithm for unmeasured disturbances in the carbon black reactor or for differences between reactors (F is usually within the range of about 0.7 to about 1.2).

The constants in the DBP algorithm are empirically determined in accordance with a known process identification procedure using regression analysis, for any given carbon black reactor geometry, in the same manner as described above for determining the algorithm constants for the iodine number algorithm. Therefore, the values of the constants will likely be different for different types of reactor geometries. The measured input variables in relation to the DBP are preferably the potassium additive solution flow rate and the feedstock flow rate. The output variable is DBP or some other suitable measure of carbon black structure. As described above for the iodine number algorithm, a series of experiments is then carried out on a carbon black reactor having the type of reactor geometry for which the algorithm will be used. Based on the experiments, a set of input and corresponding output data is collected. The regression analysis procedure is then performed on the set of data to identify the constants of the DBP algorithm. The constants in the DBP algorithm as defined in equations (15) and (16) were empirically determined pursuant to the above-described regression analysis procedure for a three-stage reactor geometry similar to that illustrated schematically in FIG. 1.

The DBP algorithm, equations (15) and (16), is employed to predict the DBP values ($DBP_p$) at spaced intervals, for example, once every second. Then, the predicted DBP values are averaged over spaced averaging intervals ($DBP_{AVG}$), for example, once every two minutes. Each average DBP value (DBP$_{AVG}$) is then employed to calculate a new potassium additive solution flow rate set point (K+S$_{NEW}$) using a DBP adjust algorithm, defined as follows:

$$K^+S_{NEW} \text{ [lb/hr]} = \text{RATIO [lb } K^+\text{S/gal. oil]} * \quad (17)$$
$$OIL_{NEW} \text{ [gal/hr]}$$

wherein:

$$\text{RATIO} = \frac{X_{NEW} \text{ [gm } K^+/100 \text{ gal. oil]}}{100 * K_{MIX} \text{ [gm } K^+/\text{lb } K^+S]} \quad (18)$$

The X$_{NEW}$ is derived from the partial derivative of the DBP algorithm (equations (15) and (16)) with respect to the concentration of the potassium ion in the feedstock (X), and is defined as follows:

$$X_{NEW} = \frac{(DBP_{GOAL} - DBP_{AVG})}{17.3 * F} + X_{AVG} \quad (19)$$
for $0 \leq X_{AVG} \leq 1$ $$X_{NEW} = \frac{(DBP_{GOAL} - DBP_{AVG})}{17.3 * F} * X_{AVG} + X_{AVG} \quad (20)$$
for $X_{AVG} > 1$ and $$X_{AVG} = \frac{K^+S_{AVG}}{OIL_{AVG}} * 100 \quad (21)$$

K$_{MIX}$ is the mixture strength of the potassium additive solution K+S, which is the grams of potassium ion (K+) per pound of potassium additive solution (K+S). X$_{NEW}$ is the new concentration of the potassium ion (K+) in the feedstock required to achieve DBP$_{GOAL}$. K+S$_{AVG}$ is the average potassium additive solution flow rate during the two-minute interval, and OIL$_{AVG}$ is the average feedstock flow rate during the two-minute interval. OIL$_{NEW}$ is the current flow rate set point for the feedstock, which is preferably adjusted in accordance with the iodine number algorithm, as described above. Therefore, by utilizing the average predicted DBP values (DBP$_{AVG}$) over the two-minute interval, the new potassium additive solution flow rate (K+S$_{NEW}$) can be determined in accordance with equation (17), in order to achieve the goal DBP value (DBP$_{GOAL}$).

The process control system of the present invention, has an additional feature, an off-line DBP laboratory measurement procedure. At spaced intervals, while the carbon black reactor is operating, samples of the carbon black produced are taken and the DBP value for each sample is measured (DBP$_{LAB}$), in a manner known to those skilled in the art. The sampling interval when the carbon black sample is taken is usually within the range of about 2 to 20 minutes. The DBP$_{LAB}$ is preferably measured in accordance with ASTM Designation: D2414-86, as mentioned above.

The measured DBP value (DBP$_{LAB}$) and its known standard deviation (SD$_{LAB}$) are determined along with the average and standard deviation (SD$_p$) of the predicted DBP values (DBP$_p$) for the period that the sample was taken. Then, depending on the measured DBP value (DBP$_{LAB}$), its standard deviation (SD$_{LAB}$), and the average and standard deviation of the predicted DBP values (DBP$_p$), the scale factor (F) of the DBP algorithm (equations (15) and (16)) is adjusted in order to calculate more correct DBP values. Thus, in accordance with the present invention, the accuracy of the DBP algorithm itself can be systematically checked against the laboratory measured DBP value (DBP$_{LAB}$) and improved while the carbon black reactor is operating.

In accordance with the sampling feature of the present invention, the best estimate of the error variance of the predicted DBP values (V$_{DP}$) and the error variance of the laboratory measured DBP value (V$_{DL}$) are determined. V$_{DL}$ is the square of the standard deviation of the laboratory measured DBP value (DBP$_{LAB}$). Because preferably only one laboratory measured DBP value is taken during each sample period, V$_{DL}$ is essentially a constant that is determined by a separate precision or reproducibility study of the DBP$_{LAB}$ measurement procedure, of a type known in the art. Therefore, V$_{DL}$ is usually updated periodically, for example, once very several months or whenever there is a change in the procedure for determining the DBP$_{LAB}$. V$_{DP}$ is the best estimate of the error variance of the current predicted DBP value (DBP$_p$), as will be described in further detail below.

Based on the error variances, V$_{DP}$ and V$_{DL}$, a filter algorithm, preferably a Kalman filter algorithm, is employed to determine a best estimate of the true DBP value during the period that the sample was taken (DBP$_{FILTER}$). The DBP$_{FILTER}$ is generated as a weighted mean between the DBP$_{LAB}$ and the average of the predicted DBP values during the period the sample was taken (DBP$_{AVG}$). The DBP Kalman filter algorithm for the DBP$_{FILTER}$ is defined as follows:

$$DBP_{FILTER} = DBP_{AVG} + K_D * (DBP_{LAB} - DBP_{AVG}) \quad (22)$$

K$_D$ is the DBP Kalman filter gain, which is essentially a weighted mean of the error variances, V$_{DP}$ and V$_{DL}$, and is defined as follows:

$$K_D = \frac{V_{DP}}{V_{DP} + V_{DL}} \quad (23)$$

Then, based upon the DBP$_{FILTER}$, the scale factor (F) of the DBP algorithm, equations (15) and (16), is adjusted (F$_{NEW}$) in order to make the DBP algorithm more correctly predict the DBP, as follows:

$$F_{NEW} = \frac{DBP_{FILTER}}{164.9 - 17.3 * (X_{AVG})} \text{ for } 0 \leq X \leq 1 \quad (24)$$

and $$F_{NEW} = \frac{DBP_{FILTER}}{147.6 - 17.3 * \ln (X_{AVG})} \text{ for } X > 1 \quad (25)$$

X$_{AVG}$ is the average concentration of potassium additive solution (K+S) in the feedstock, as defined in equation (21), during the period the sample was taken. The new scale factor (F$_{NEW}$) is then substituted into the DBP algorithm (equations (15) and (16)) to replace the previous scale factor (F) and thus adjust the algorithm to more accurately predict the DBP.

The best estimate of the true current error variance of the predicted DBP$_{value}$ (V$_{DP}$(k+1)) at time interval (k+1), which is used in equation (23) to determine the current DBP Kalman filter gain (K$_D$), is defined as follows:

$$V_{DP}(k+1) = V_{DE}(k) + V_{DM}(k+1) \quad (26)$$

wherein:

$V_{DP}(k+1)$ is the best estimate of the true current error variance of the current predicted DBP value at time interval (k+1);

$V_{DE}$ is the error variance of the previous optimum DBP estimate (DBP$_{FILTER}$) at time interval (k); and $V_{DM}(k+1)$ is the error variance of the predicted DBP values (DBP$_p$) at time interval (k+1) measured over the last sample period.

The new DBP Kalman filter gain $K_D(k+1)$ is then determined as a weighted mean of the error variances of the current predicted DBP values (DBP$_p$) and the current laboratory measured DBP value (DBP$_{LAB}$) as follows:

$$K_D(k+1) = \frac{V_{DP}(k+1)}{[V_{DP}(k+1) + V_{DL}(k+1)]} \quad (27)$$

$V_{DL}(k+1)$ is the error variance of the current laboratory measured DBP value (DBP$_{LAB}$) and is defined as follows:

$$V_{DL}(k+1) = [PSD_{LAB}/100]^2 \cdot DBP_{GOAL} \quad (28)$$

Here, PSD$_{LAB}$ is the present standard deviation of the laboratory DBP which is determined by a precision or reproducibility study, known in the art. Therefore, the new DBP Kalman filter gain ($K_D(k+1)$) is substituted into equation (22) above to solve for the new optimum estimated DBP value (DBP$_{FILTER}$). The DBP$_{FILTER}$ is then substituted into equations (24) or (25) above to solve for the new scale factor ($F_{NEW}$) to make the DBP algorithm (equations (15) and (16)) more correctly predict the DBP.

The error variance of the new optimum estimated DBP value ($V_{DE}(k+1)$ to be used in determining $V_{DP}(k+1)$ at the end of the next sample period ($V_{DE}(k)$ in equation (26) above) is then determined as follows:

$$V_{DE}(k+1) = \frac{V_{DP}(k+1) \cdot V_{DL}(k+1)}{V_{DP}(k+1) + V_{DL}(k+1)} \quad (29)$$

In accordance with another embodiment of the present invention, the process control system further incorporates a CUSUM ("cumulative sums") procedure for monitoring the values of the output variables controlled, such as iodine number and/or DBP. The CUSUM compensates for trends in either the iodine number or DBP that might be the result of unmeasured disturbances on the carbon black reactor not completely compensated for by the iodine number algorithm, DBP algorithm, or the respective Kalman filter algorithms. Therefore, a CUSUM monitors the I$_2$No.$_{LAB}$ and a CUSUM monitors the DBP$_{LAB}$ every time each output variable is measured to determine if there is a shift in the mean of either value that is sufficient to require a further adjustment in the process.

Each CUSUM employs two cumulative sums, a high side sum ($S_{H(i)}$) and a low side sum ($S_{L(i)}$), to test the I$_2$No.$_{LAB}$ and the DBP$_{LAB}$, respectively, to determine if there is an undesirable trend. When the CUSUMs are reset, each cumulative sum ($S_{H(i)}$ and $S_{L(i)}$) is set equal to zero. The two sums are as follows:

$$S_{H(i)} = Max[O, S_{H(i-1)} + Y_i - (GOAL + k)] \quad (30)$$

$$S_{L(i)} = Min[O, S_{L(i-1)} + Y_i - (GOAL - k)] \quad (31)$$

wherein:

$S_{H(i-1)}$ is a summation of all previous high sums since the last CUSUM reset;

$S_{L(i-1)}$ is the summation of all previous low side sums since the last CUSUM reset;

$Y_i$ is the current laboratory measured value of the output variable controlled and, therefore, in accordance with the previous embodiments it may be I$_2$No.$_{LAB}$ or DBP$_{LAB}$;

GOAL is the goal value of the output variable controlled and, therefore, in accordance with the previous embodiments it may be I$_2$No.$_{GOAL}$ or DBP$_{GOAL}$; and k is the allowable slack in the controlled output variable, which is usually in the range of about one standard deviation or within which about 68% of the laboratory measured values of the respective controlled output variable (such as I$_2$No.$_{LAB}$ or DBP$_{LAB}$) will fall.

A decision interval (−h,h) is set for each controlled output variable, the exact value of which is chosen based on experience with the particular carbon black reactor used, but which is usually near the tolerance limits set for that output variable. For example, a typical value of h for iodine number or DBP might be 5. Therefore, the decision interval h would be 5 iodine number units or DBP units on either side of the value of the I$_2$No.$_{GOAL}$ or DBP$_{GOAL}$, respectively.

After each sample of carbon black is taken and the laboratory measured values for iodine number (I$_2$No.$_{LAB}$) and/or DBP (DBP$_{LAB}$) are determined, those values are each substituted into equations (30) and (31) for ($Y_i$) The two cumulative sums, $S_{H(i)}$ and $S_{L(i)}$, are then computed for both the I$_2$No.$_{LAB}$ and the DBP$_{LAB}$. Then, if $S_{H(i)} \geq h$ or, if $S_{L(i)} \leq -h$, for either the iodine number or DBP, an alarm signal is generated for the respective output variable. If an alarm signal is generated, then the operator is notified to increase the sampling frequency of the carbon black produced, usually at least by a factor of two. If an alarm signal is generated for the iodine number and/or DBP, respectively, then the Kalman gain ($K_I$) for the iodine number algorithm, and/or the DBP Kalman filter gain ($K_D$) for the DBP algorithm, are each set equal to one, respectively. If after the next carbon black sample is taken, the I$_2$No.$_{LAB}$ or DBP$_{LAB}$ falls within ±k of the I$_2$No.$_{GOAL}$ or DBP$_{GOAL}$, respectively, then the CUSUM is reset by setting the cumulative sums $S_{H(i-1)}$ and $S_{L(i-1)}$ to zero for the respective variable. However, if an alarm signal continues to be generated, then the Kalman filter gain ($K_I$ or $K_D$) for the respective output variable is set equal to one until the laboratory measured value falls within ±k of the goal value for that variable.

Figure 2:
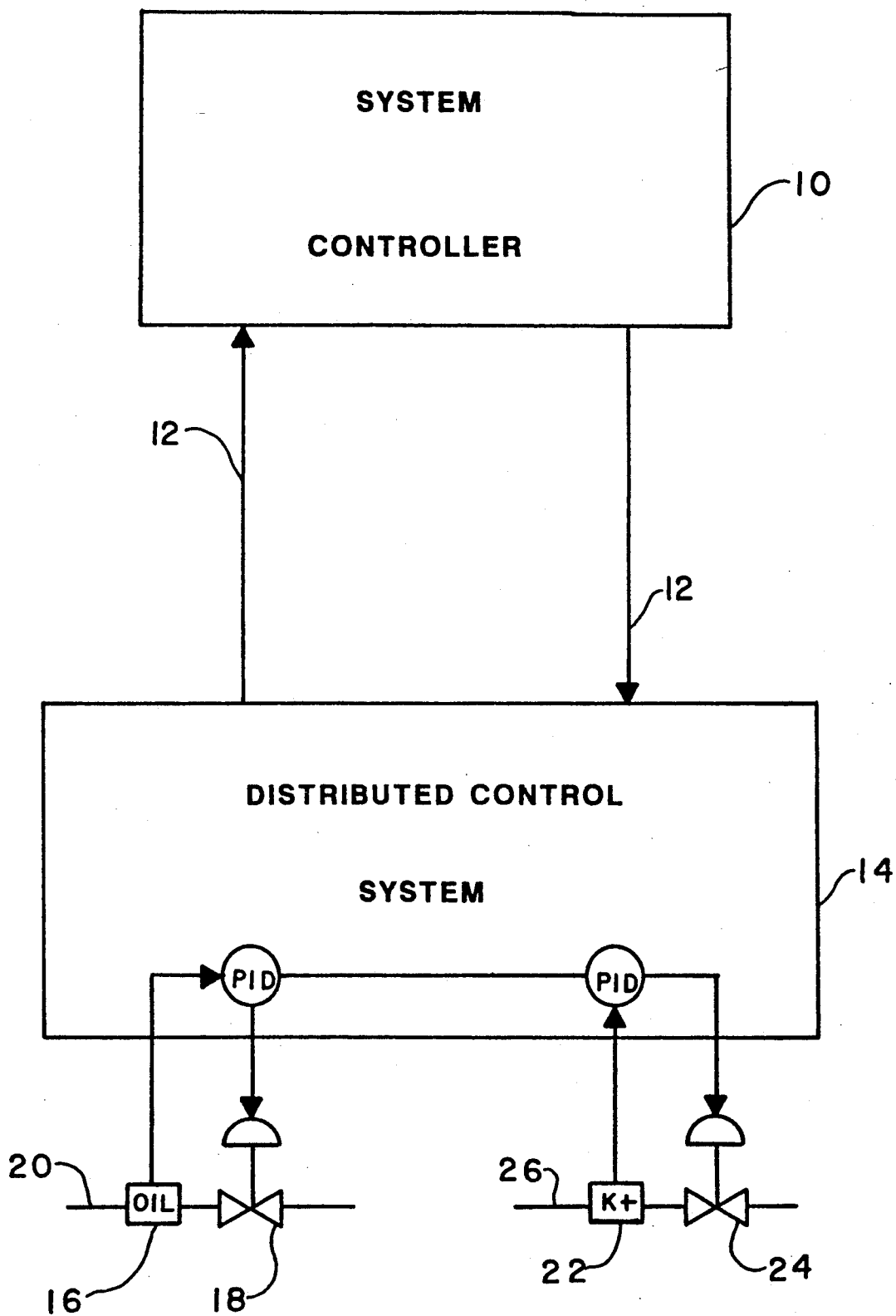
FIG. 2 illustrates schematically the hardware components of the process control system of the present invention.

In FIG. 2, the hardware components of the process control system of the present invention are illustrated schematically. The process control system comprises a system controller indicated generally as 10. The system controller 10 is a type known to those skilled in the art, and preferably is a minicomputer, such as a VAX minicomputer as described above. The system controller 10 is coupled through a bus 12 to a distributed control system 14. The distributed control system 14 is also a type known to those skilled in the art, such as a Fisher PRoVOX Instrumentation System, manufactured by Fisher Controls International, Inc., of Marshalltown, Iowa. The distributed control system 14 is, in turn, coupled through a PID algorithm (PID) to an oil flow meter 16, and an automatically adjustable flow valve 18. As described above, the oil flow meter 16 is preferably a Coriolis-type flow meter. The oil flow valve 18 is mounted upstream or downstream from the oil flow meter 16 in a feedstock line 20 of the carbon black reactor. Therefore, the distributed control system 14 controls the operation of the valve 18 in order to automatically adjust the feedstock flow rate (OIL) to achieve the goal iodine number ($I_2No._{GOAL}$), as will be described in further detail below. The distributed control system 14 is also coupled through a PID algorithm (PID) to a potassium additive solution flow meter 22, and an automatically adjustable flow valve 24. The flow meter 22 is preferably a Coriolis-type flow meter like the oil flow meter 16. The flow valve 24 is mounted upstream or downstream from the flow meter 22 in a potassium additive solution line 26 of the carbon black reactor. Therefore, the distributed control system 14 also controls the operation of the valve 22 in order to automatically adjust the potassium additive solution flow rate (K+S) to achieve the goal DBP value ($DBP_{GOAL}$), as will be described in further detail below.

Figure 3:
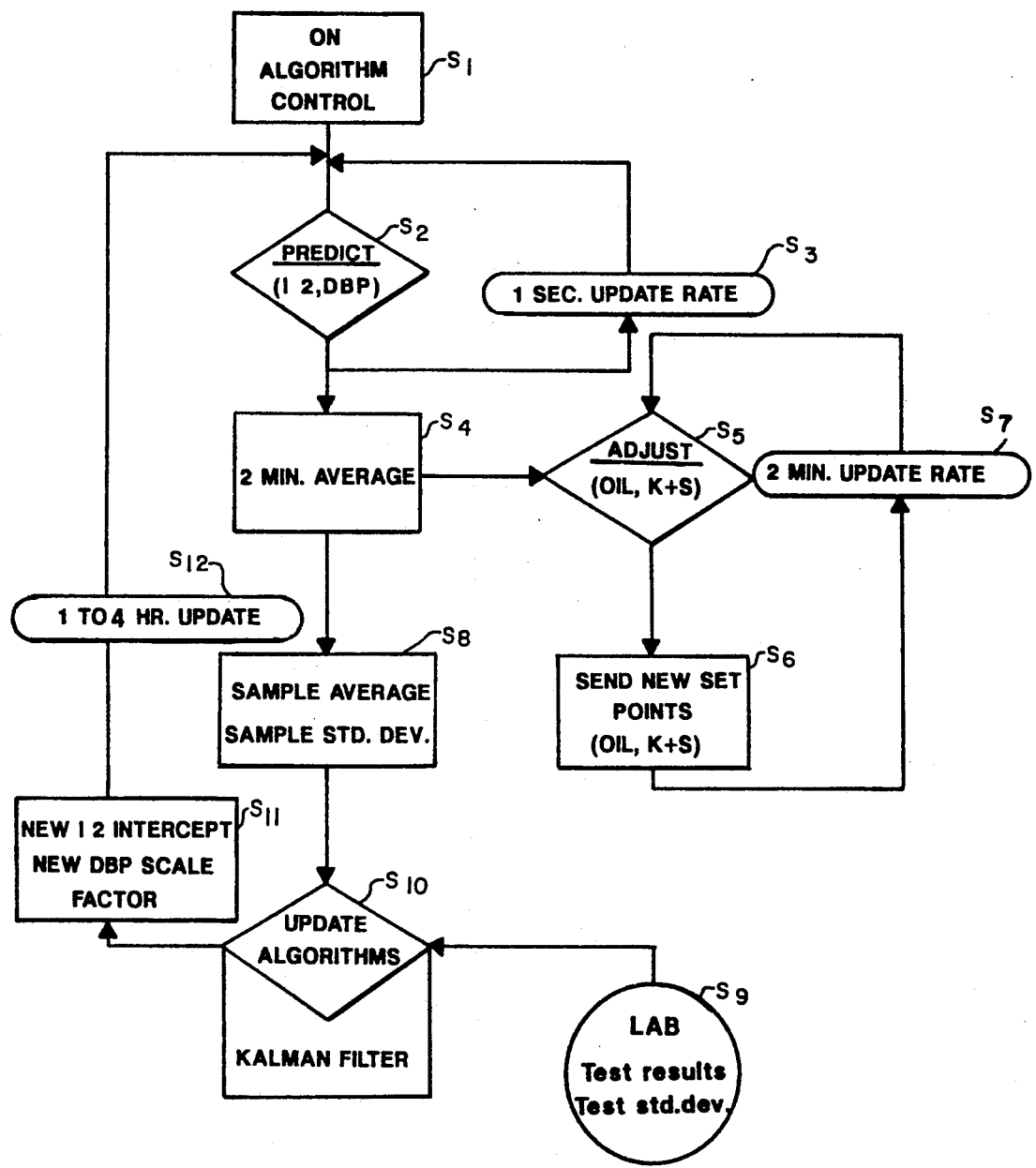
FIG. 3 is a flow chart that illustrates conceptually the procedures of the process control system of the present invention for controlling the iodine number and/or the DBP.

Turning to FIG. 3, a flow chart is illustrated that conceptually describes the procedures of the carbon black process control system of the present invention. The labels $S_1$ through $S_{12}$ indicate step 1 through step 12. When the process control system is operating, as indicated at $S_1$, the distributed control system 14 generates a predicted iodine number ($I_2No._p$) and a predicted DBP value ($DBP_p$), as indicated at $S_2$, in accordance with the iodine number algorithm and DBP algorithm, respectively, as described above. Preferably, the iodine number algorithm and, therefore, the equations for the feedforward input variables are embodied as subroutines in the distributed control system 14. Likewise, the equations of the DBP algorithm are also preferably carried out by the distributed control system 14 in subroutines. After each $I_2No._p$ and $DBP_p$ is calculated, they are each then stored in computer memory in the system controller 10. The distributed control system 14 calculates both the $I_2No._p$ and the $DBP_p$ about once every second based on the current input variable readings, as indicated at $S_3$. Each updated $I_2No._p$ and $DBP_p$ is then stored in memory in the system controller 10. Then, as indicated at $S_4$, the $I_2No._p$ and $DBP_p$ values stored in the computer memory over each two-minute interval, are averaged, $I_2No._{AVG}$ and $DBP_{AVG}$, by the distributed control system 14, and stored in the computer memory.

Based upon the $I_2No._{AVG}$ over the two-minute interval, the new feedstock flow rate ($OIL_{NEW}$) is then determined by the distributed control system 14, as indicated at $S_5$. Likewise, based upon the $DBP_{AVG}$ over the two-minute interval, the new potassium additive solution flow rate ($K+S_{AVG}$) is also determined. Equations (5) through (7), and equations (17) through (21), as described above, are preferably embodied as subroutines in the distributed control system 14 for determining both the new feedstock flow rate ($OIL_{NEW}$) and the new potassium additive solution flow rate ($K+S_{NEW}$), respectively. Based on the new feedstock flow rate ($OIL_{NEW}$) and the new potassium additive solution flow rate ($K+S_{NEW}$), the distributed control system 14 then determines the degree to adjust the valve 18 and the valve 24 by employing PID algorithms, as will be described further below. The new feedstock flow rate ($OIL_{NEW}$) and the new potassium additive solution flow rate ($K+S_{NEW}$) are then each updated every two minutes. The valves 18 and 24 are then, in turn, adjusted every two minutes based on the new $I_2No._{AVG}$ and $DBP_{AVG}$, respectively, to achieve the new flow rates, as indicated at $S_7$.

The first step in the off-line laboratory measurement features of the present invention is indicated at $S_8$, which indicates that the system controller 10 computes the average and the standard deviation of both the $I_2No._p$ and $DBP_p$ calculated every second (or other spaced interval) during the period that the carbon black sample is taken. The carbon black produced is sampled at spaced intervals, for example, usually within the range of about every one to four hours, and both the iodine number and the DBP of the sample is measured in a laboratory ($I_2No._{LAB}$ and $DBP_{LAB}$), as indicated at $S_9$. As mentioned above, the carbon black sampling interval is usually within the range of about 2 to 20 minutes. Then, the new system intercept (KO) for the iodine number algorithm is updated by the system controller 10, based on the $I_2No._{LAB}$ and the $I_2No._{AVG}$ calculated during the period that the sample was taken, as indicated at $S_{10}$. Preferably, equations (8) through (14), as described above, are embodied as subroutines in the system controller 10. Likewise, the scaling factor (F) is also adjusted based on the $DBP_{LAB}$ and $DBP_{AVG}$ during the period that the sample was taken. Preferably, equations (22) through (29), as described above, are also carried out as subroutines in the distributed control systems 14. The new system intercept ($KO_{NEW}$) is then used to update the iodine number algorithm for determining more accurate predicted iodine numbers ($I_2No._p$) until the next carbon black sample is taken, as indicated at $S_{11}$. Likewise, the new scaling factor ($F_{NEW}$) is used to update the DBP algorithm for determining more accurate DBP values until the next carbon black sample is taken, as also indicated at $S_{11}$. As indicated at $S_{12}$, the iodine number algorithm and DBP algorithm are each updated whenever a carbon black sample is taken and, therefore, within the range of about every 1 to 4 hours.

Figure 4:
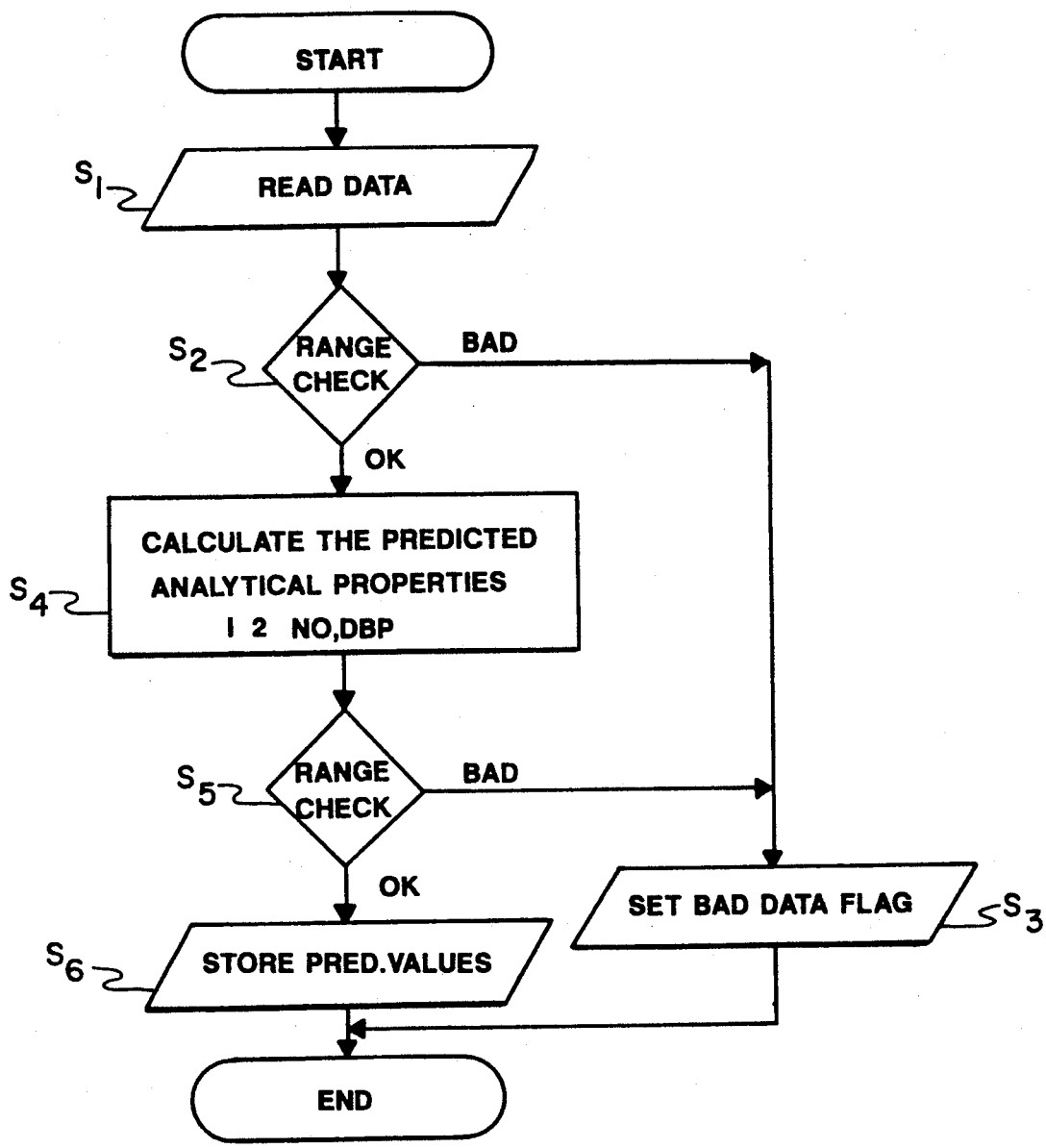
FIG. 4 is a flow chart that illustrates conceptually the procedures of the distributed control system of FIG. 2 in predicting the iodine number and the DBP in accordance with the present invention.

Turning to FIG. 4, a flow chart is illustrated that describes conceptually the procedures of the distributed control system 14 in predicting both the iodine number $I_2No._p$ in accordance the iodine number algorithm, and the $DBP_p$ in accordance the DBP algorithm, as described above. The distributed control system 14 first reads the input data necessary to calculate the feedforward input variables for the iodine number algorithm, and the input variable for the DBP algorithm, as indicated at $S_1$. The input variables for the iodine number algorithm, include the feedstock flow rate, gas flow rate, air flow rate, air preheat temperature, and air humidity. The ATBG (fuel quality) is a calculated control variable and the ATBO (feedstock quality) is essentially a constant control variable, as described above. The input variables for the DBP algorithm are the potassium additive solution flow rate and the feedstock flow rate.

After reading the input data, the distributed control system then compares the input data to a permissible range of values for each variable, as indicated at $S_2$. If any value falls outside of its permissible range (BAD), then a bad data flag, which is a digital signal, is set, as indicated at $S_3$. If the bad data flag is set, then the $I_2No._p$ and/or the $DBP_p$ is not calculated based on that data. If all the data does fall within the permissible ranges, then both an $I_2No._p$ and $DBP_p$ are calculated based on that set of input data by employing the iodine number algorithm and the DBP algorithm, respectively, as indicated at $S_4$. Both the $I_2No._p$ and $DBP_p$ are each then compared to a realistic range within which each output variable should fall, as indicated at $S_5$. If either the $I_2No._p$ or $DBP_p$ is not within the permissible range, then bad data flag is set and the current values for $I_2No._p$ and/or $DBP_p$ are not used, depending if one or both falls outside its respective permissible range. If the $I_2No._p$ or $DBP_p$ do fall within their permissible ranges, then their values are stored in the computer memory of the system controller 10, as indicated at $S_6$, and are later (at the end of the spaced interval) each used to update the feedstock flow rate and the potassium additive solution flow rate, respectively.

Figure 5:
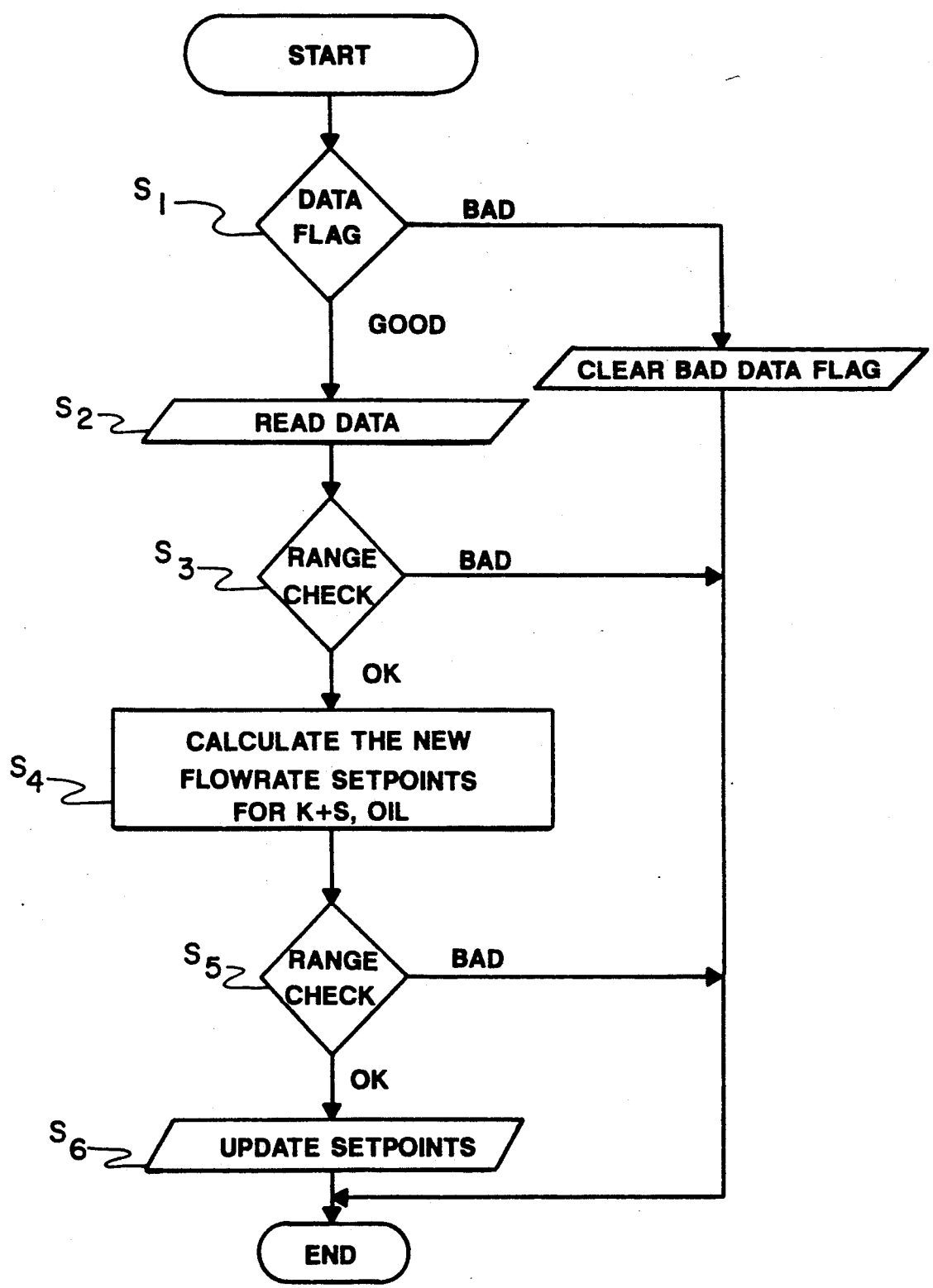
FIG. 5 is a flow chart that illustrates conceptually the procedures of the distributed control system of FIG. 2 for adjusting the feedstock flow rate and the potassium additive solution flow rate to achieve the goal iodine number and goal DBP, respectively, in accordance with the present invention.

Turning to FIG. 5, a flow chart is illustrated that describes conceptually the procedures of the distributed control system 14 for adjusting both the feedstock flow rate and the potassium additive solution flow rate. As indicated at $S_1$, if the bad data flag was set during the iodine number and/or DBP prediction procedures (BAD), as illustrated at $S_3$ in FIG. 4, then the bad data flag is cleared and the adjustment procedures as illustrated in FIG. 5 are not implemented for that spaced interval, for whichever algorithm had the bad input data. However, if the bad data flag was not set during the two-minute interval, then the distributed control system 14 reads the input data for determining the new feedstock set point ($OIL_{NEW}$) and/or the potassium additive solution set point ($K+S_{NEW}$), as indicated at $S_2$. The input data for $OIL_{NEW}$ includes the $AIR_{AVG}$, $GAS_{AVG}$, ATBG, ATBO and $OAC_{AVG}$, as defined in equation (7). The input data for the $K+S_{NEW}$ includes the $K+S_{AVG}$, $OIL_{AVG}$, $DBP_{AVG}$, and $X_{AVG}$, as defined in equations (17) through (21).

The input data are then compared to a permissible range of values for each term, as indicated at $S_3$. If any of the values fall outside of their respective permissible ranges, then the bad data flag is set (BAD). Accordingly, the feedstock flow rate set point ($OIL_{NEW}$) and the potassium additive solution set point ($K+S_{NEW}$) are not adjusted for that spaced interval, if the input data for one and/or both is bad. If all of the values fall within their permissible ranges, then the $OIL_{NEW}$ and $K+S_{NEW}$ are each updated as described above, as indicated at $S_4$. Both the $OIL_{NEW}$ and $K+S_{NEW}$ are then each compared to a permissible range of values, as indicated at $S_5$. If either the $OIL_{NEW}$ or the $K+S_{NEW}$ falls outside of its respective permissible range (BAD), then the procedures end for that respective term and its flow rate is not adjusted. If the $OIL_{NEW}$ and $K+S_{NEW}$ do fall within their permissible ranges, then the values for $OIL_{NEW}$ and $K+S_{NEW}$ are each processed through a PID algorithm to update the feedstock flow rate and potassium additive solution flow rate, respectively, as indicated at $S_6$.

Figure 6:
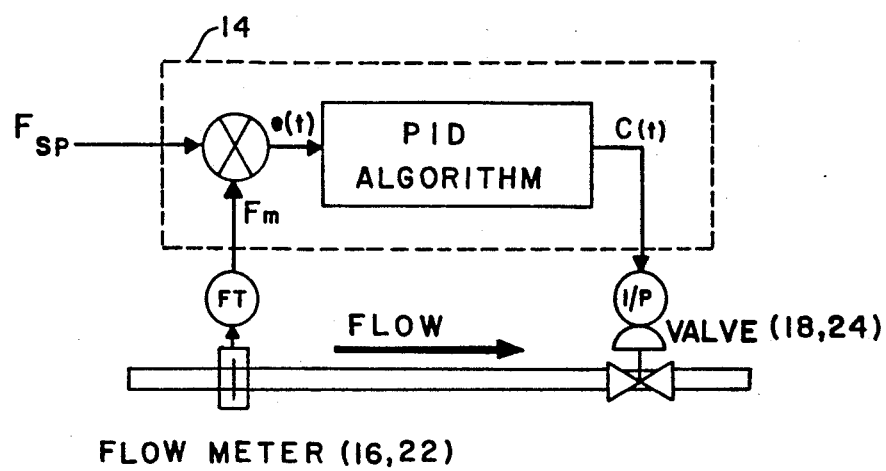
FIG. 6 illustrates schematically a PID algorithm employed in accordance with the present invention for adjusting the new feedstock flow rate and the new potassium additive solution flow rate to achieve the goal iodine number and the goal DBP, respectively.

Turning to FIG. 6, a typical PID algorithm which is preferably employed for adjusting the new feedstock flow rate ($OIL_{NEW}$) or for adjusting the new potassium additive solution flow rate ($K+S_{NEW}$), is illustrated schematically. The flow meter for the feedstock 16 and the flow meter for the potassium additive solution 22 are each coupled respectively to a flow transmitter (FT). Each flow transmitter (FT) is, in turn, coupled to the distributed control system 14 and transmits a signal ($F_m$) corresponding to the measured flow rate as sensed by its respective flow meter. The signals for the new flow rate set points for the feedstock and the potassium additive solution ($F_{sp}$) are then each compared to their respective measured flow rate signals ($F_m$) as generated by the flow meters. Based on the respective comparisons, an error signal (e(t)), which is equal to the respective flow rate set point signal ($F_{sp}$) minus the respective measured flow rate signal ($F_m$), is generated for each respective flow rate. Then, based on the respective error signals (e(t)), a respective PID algorithm, which is known to those skilled in the art, generates an output signal (c(t)) that corresponds to the adjustment that should be made to the respective flow valves 18 or 24 to achieve the flow rate set points. Each output signal is then sent to a respective current to pneumatic converter (I/P). The current to pneumatic converters (I/P) are each coupled respectively to the oil flow valve 18 and the potassium additive solution flow valve 24 for adjusting each respective valve. The current to pneumatic converters (I/P) therefore each generate a pressurized output corresponding to the respective PID output signal (c(t)) that, in turn, adjusts its respective valve to achieve the flow rate set point. Therefore, each PID algorithm continues to generate changes in the output signal (c(t)) until there is no longer an error signal (e(t)), and thus the flow rate set points are achieved.

Figure 7:
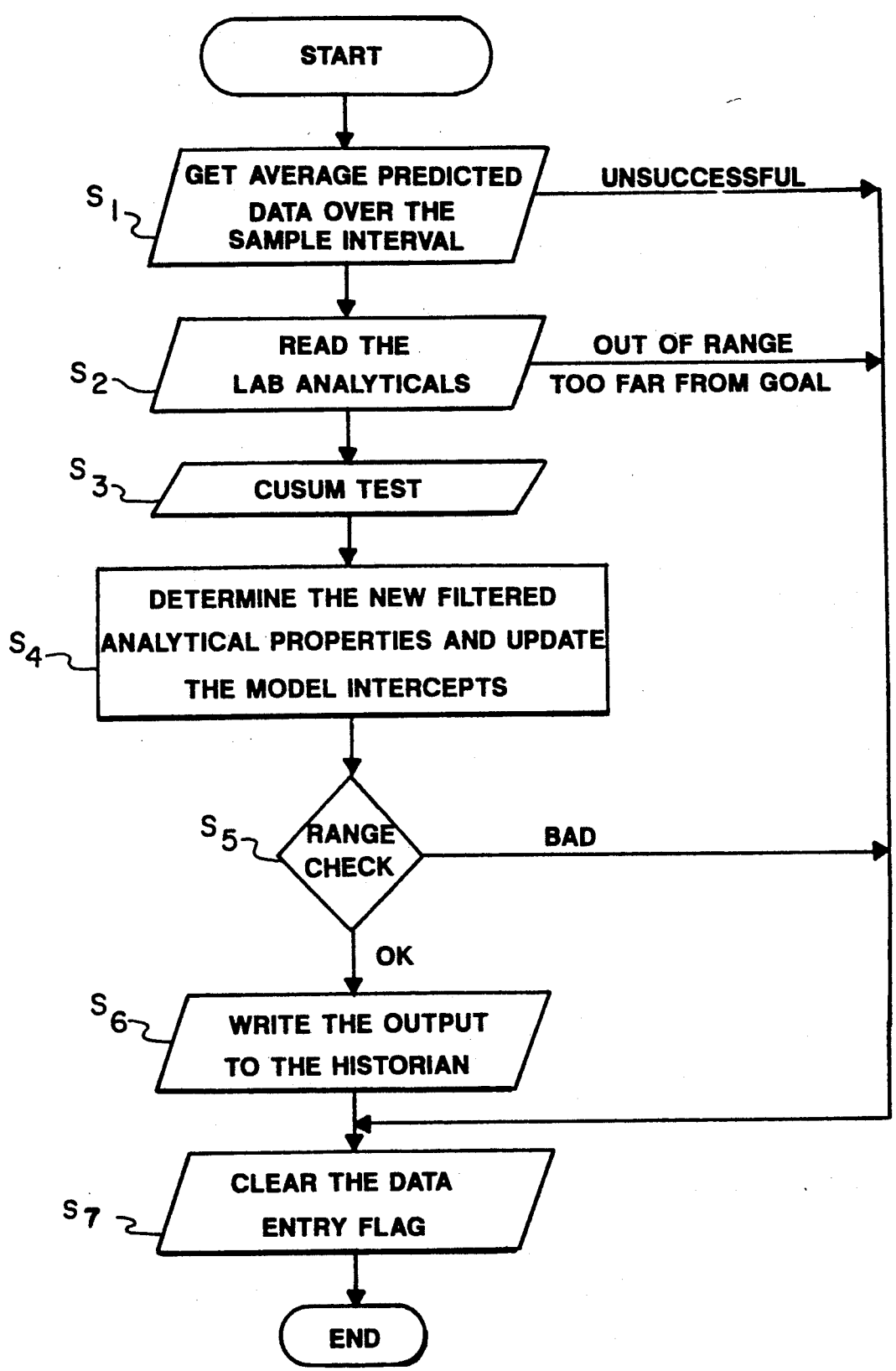
FIG. 7 is a flow chart that illustrates conceptually the procedures of the system controller of FIG. 2 for adjusting the iodine number algorithm and the DBP algorithm at the end of each carbon black sample period in accordance with the present invention.

Turning to FIG. 7, a flow chart is illustrated that describes conceptually the procedures of the system controller 10 for updating the system intercept (KO) of the iodine number algorithm and/or the scale factor (F) of the DBP algorithm at the end of each carbon black sample period. As indicated at $S_1$, the system controller recalls from memory the $I_2No._p$ and $DBP_p$ values calculated and stored during the period that the sample was taken. If the system controller cannot properly recall the data (Unsuccessful), then the algorithms are not adjusted. The system controller 10 then reads the values for the current $I_2No._{LAB}$ and the $DBP_{LAB}$ and compares them to a permissible range of values. If either value is out of range, then its respective algorithm is not adjusted. The system controller 10 then employs the CUSUM procedure which determines the current sums, $S_{H(i)}$ and/or $S_{L(i)}$, for the current $I_2No._{LAB}$ and $DBP_{LAB}$ values, as indicated at $S_3$. If either $S_{H(i)} \geq h$ or $S_{L(i)} \leq -h$ for either measured output variable ($I_2No._{LAB}$ or $DBP_{LAB}$), the system controller generates an alarm signal. If an alarm signal is generated, then the Kalman filter gain ($K_I$) for the iodine number algorithm and/or the DBP Kalman filter gain ($K_D$) for the DBP algorithm are set equal to 1, depending on whether an alarm signal is generated for one or both output variables. Therefore, the new system intercept ($KO_{NEW}$) for the iodine number algorithm, and/or the new scale factor ($F_{NEW}$) for the DBP algorithm, are both based solely on the laboratory measured values of $I_2No._{LAB}$ and $DBP_{LAB}$, respectively. However, if an alarm signal is not generated, then the system controller determines the new filtered analytical properties, $I_2No._{FILTER}$ and $DBP_{FILTER}$, and, in turn, adjusts the system intercept constant (KO) and the scale factor (F) to update the iodine number algorithm and DBP algorithm, respectively, as indicated at $S_4$. Then, as indicated at $S_5$, the values for the new system intercept ($KO_{NEW}$) and scale factor ($F_{NEW}$) are compared to a permissible range for each value. If either value is out of range, then it is not used to update its respective algorithm. If the values for $KO_{NEW}$ and $F_{NEW}$ are each within range, then they are each stored in memory, as indicated at $S_6$. Upon storing the values in memory, the system controller 10 then clears the data entry flag, as indicated at $S_7$, until the end of the next sample period.

What is claimed is:

1. In a process for producing carbon blacks in a carbon black reactor, a method of controlling the production of carbon black comprising the following steps:
   a) determining the input variables utilizes in the production of carbon black and the corresponding output variables indicative of the properties of the carbon black product to be controlled in the carbon black production process;
   b) generating a predicting algorithm for predicting at least one output variable based on at least one input variable, said at least one input variable being selected from the group including the fuel flow rate, the feedstock flow rate, the oxidant flow rate, the oxidant humidity, the oxidant preheat temperature, the first stage fuel quality, the feedstock quality, and the concentration of potassium in the feedstock;
   c) pyrolyzing a hydrocarbon feedstock with hot combustion gases in the carbon black reactor to produce carbon black;
   d) measuring at time spaced measuring intervals at least one of said input variables while the carbon black reactor is operating;
   e) employing said predicting algorithm to predict at time spaced predicting intervals at least one of said output interval and generating a first signal indicative of said predicted output variable;
   f) determining at spaced averaging intervals an average value of said at least one predicted output variable over said averaging interval and generating a second signal indicative of the average value of said at least one predicted output variable;
   g) selecting a goal value of said at least one predicted output variable, and comparing said second signal to a third signal indicative of said goal value;
   h) adjusting while the reactor is operating at least one of said input variables pursuant to an adjusting algorithm if there is a difference between said second and third signals, at least one of said input variables adjusted being selected from the group including the feedstock flow rate, the fuel flow rate, the oxidant flow rate, the oxidant preheat temperature, the oxidant humidity, and the concentration of potassium in the feedstock, to achieve said goal value of said at least one output variable and thereby obtain a substantially consistent quality of carbon black;
   i) repeating steps d through h
   j) sampling at time spaced intervals the carbon black produced while the carbon black reactor is operating;
   k) measuring said at least one output variable predicted by said predicting algorithm from the sample of carbon black while the carbon black reactor is operating;
   l) adjusting said predicting algorithm based on a comparison between said measured value of said at least one output variable and said predicted value of said output variable, in order to more correctly predict said at least one output variable; and
   m) repeating steps d through l.

2. A method as defined in claim 1, wherein said predicted output variable is the surface area and said predicting algorithm includes at least one feed forward input variable selected from the group including the overall combustion, the primary combustion, the combustion air rate, the combustion air preheat temperature, and the air absolute humidity.

3. A method as defined in claim 2, wherein said predicted output variable is the iodine number.

4. A method as defined in claim 1, wherein said predicted output variable is the iodine number and said predicting algorithm predicts the iodine number based on a plurality of input variables.

5. A method as defined in claim 4, wherein said plurality of input variables includes the oxidant flow rate, the fuel flow rate, the feedstock flow rate, the oxidant preheat temperature, and the oxidant humidity.

6. A method as defined in claim 1, wherein said predicted output variable is the iodine number and said adjusted input variable is the feedstock flow rate.

7. A method as defined in claim 1, wherein said predicted output variable is the structure of the carbon black and said input variable employed by said predicting algorithm for predicting said output variable is the concentration of potassium in the feedstock.

8. A method as defined in claim 7, wherein said predicted output variable is the DBP.

9. A method as defined in claim 1, wherein said predicted output variable is the structure of the carbon black and said adjusted input variable is the concentration of potassium in the feedstock.

10. A method of controlling the production of carbon black as described in claim 6, wherein said feedstock flow rate is adjusted by utilizing the relationship between the goal iodine number minus the average value of the predicted iodine number over said spaced averaging interval and the difference between the new overall combustion required to achieve the goal iodine number minus the average value of the overall combustion during said spaced averaging interval.

11. A method of controlling the production of carbon black as described in claim 9, wherein said concentration of potassium in the feedstock is adjusted by utilizing the difference between the average value of said predicted output variable during said spaced averaging interval and the goal value of said output variable.

12. A method of controlling the production of carbon black as described in claim 1, wherein said predicting algorithm is adjusted by utilizing a weighted mean of the best estimate of the error variance of the current predicted value of said at least one carbon black output variable and the error variance of the measured value of said at least one output variable.

13. A method of controlling the production of carbon black as described in claim 12, wherein said predicting algorithm is adjusted by employing at least one second algorithm for determining a new estimated value of said at least one output variable by utilizing said weighted mean of error variances and the difference between said measured value of said at least one output variable and said average value of said predicted values of said at least one output variable during the period the sample was taken, and said new estimated output variable provided by said at least one second algorithm is employed to adjust said at least one algorithm to more correctly predict said at least one output variable.

14. A method of controlling the production of carbon black as described in claim 13, wherein
    said output variable is the iodine number.

15. A method of controlling the production of carbon black as described in claim 13, wherein
    said output variable is the DBP.

16. A method of controlling the production of carbon black as described in claim 1, wherein said at least one output variable is predicted at spaced predicting intervals within the range of about one second to twenty seconds.

17. A method of controlling the production of carbon black as described in claim 1, wherein said average value of said at least one predicted output variable is determined at spaced averaging interval within the range of about one minute to three minutes.

18. A method of controlling the production of carbon black as described in claim 17, wherein said at least one input variable is adjusted each time said average value of said at least one predicted output variable is determined.

19. A method of controlling the production of carbon black as described in claim 18, wherein said at least one output variable is the iodine number.

20. A method of controlling the production of carbon black as described in claim 19, wherein said at least one input variable is the feedstock flow rate.

21. A method of controlling the production of carbon black as described in claim 18, wherein said at least one output variable is the DBP.

22. A method of controlling the production of carbon black as described in claim 21, wherein said at least one input variable is the potassium additive solution flow rate.

23. A method of controlling the production of carbon black as described in claim 1, said method further comprising the following steps:

monitoring said measured values of said at least one carbon black output variable in order to detect a shift in the mean of said at least one output variable.

24. A method of controlling the production of carbon black as described in claim 23, wherein said measured values of said at least one output variable are monitored by summing the difference between the current measured value of said output variable and the goal value of said output variable plus or minus a slack value, and then comparing the value of said summation to a decision interval, such that if the value of said summation falls outside of said decision interval, an alarm signal is generated.

25. A method of controlling the production of carbon black as described in claim 24, wherein said slack value is determined so that when added to and subtracted from the goal value of said at least one output variable, the two resulting values substantially define a range within about one standard deviation or within which about 68% of the measured values of said at least one output variable fall.

26. A method of controlling the production of carbon black as described in claim 24, wherein
said decision interval defines a permissible range of values on either side of the goal value of said at least one output variable.

27. A method of controlling the production of carbon black as described in claim 1, wherein said spaced intervals for sampling the carbon black produced are within the range of about 0.5 hours to about 5 hours.

28. A method of controlling the production of carbon black, as recited in claim 27, wherein
the time period of taking each carbon black sample is within the range of about 1 minute to about minutes.

* * * * *